(12) United States Patent
Reiner

(10) Patent No.: US 8,301,461 B2
(45) Date of Patent: Oct. 30, 2012

(54) METHOD AND APPARATUS FOR GENERATING A RADIOLOGIST QUALITY ASSURANCE SCORECARD

(76) Inventor: Bruce Reiner, Seaford, DE (US)

( * ) Notice: Subject to any disclaimer, the term of this patent is extended or adjusted under 35 U.S.C. 154(b) by 1395 days.

(21) Appl. No.: 11/699,344

(22) Filed: Jan. 30, 2007

(65) Prior Publication Data

US 2007/0232868 A1    Oct. 4, 2007

Related U.S. Application Data

(60) Provisional application No. 60/762,859, filed on Jan. 30, 2006, provisional application No. 60/763,353, filed on Jan. 31, 2006, provisional application No. 60/763,357, filed on Jan. 31, 2006, provisional application No. 60/771,482, filed on Feb. 9, 2006, provisional application No. 60/771,484, filed on Feb. 9, 2006.

(51) Int. Cl.
*G06Q 10/00* (2006.01)
(52) U.S. Cl. ............ 705/2; 382/115; 382/128; 382/132
(58) Field of Classification Search .................. 705/2, 3; 434/262; 713/193
See application file for complete search history.

(56) References Cited

U.S. PATENT DOCUMENTS

| | | | | |
|---|---|---|---|---|
| 5,933,136 A * | 8/1999 | Brown | ........................ | 715/741 |
| 6,669,482 B1 * | 12/2003 | Shile | ............................ | 434/262 |
| 7,234,064 B2 * | 6/2007 | Menschik et al. | ............ | 713/193 |
| 2002/0186818 A1 * | 12/2002 | Arnaud et al. | ................ | 378/165 |
| 2002/0188652 A1 * | 12/2002 | Goldhaber et al. | ........... | 709/201 |
| 2003/0212580 A1 | 11/2003 | Shen | | |
| 2004/0122702 A1 * | 6/2004 | Sabol et al. | ....................... | 705/2 |
| 2005/0027995 A1 * | 2/2005 | Menschik et al. | ............ | 713/193 |
| 2005/0203775 A1 | 9/2005 | Chesbrough | | |
| 2007/0011024 A1 * | 1/2007 | Dale et al. | ........................ | 705/2 |
| 2009/0089079 A1 * | 4/2009 | Goldhaber et al. | ............... | 705/2 |

* cited by examiner

*Primary Examiner* — Valerie Lubin
(74) *Attorney, Agent, or Firm* — Jean C. Edwards, Esq.; Edwards Neils PLLC

(57) ABSTRACT

The present invention provides a quality assurance system and method that generates a quality assurance (QA) scorecard for radiologists that use digital devices in a radiological-based medical imaging study. According to one embodiment, client computers, servers, imaging devices, databases, and/or other components may be coupled to provided a unified data collection system. According to one embodiment, systems and methods are provided that analyze various parameters that are derived from the unified data collection system to calculate a QA score for the radiologist. The QA score provides a combined subjective and objective feedback system that includes performance evaluations from other users, including clinicians and patients. According to one embodiment, the feedback may be provided in real-time.

22 Claims, 4 Drawing Sheets

METHOD AND APPARATUS FOR GENERATING A RADIOLOGIST QUALITY ASSURANCE SCORECARD

CROSS-REFERENCE TO RELATED APPLICATIONS

This application claims priority from U.S. Provisional Patent Application No. 60/762,859, dated Jan. 30, 2006, U.S. Provisional Patent Application No. 60/763,353, dated Jan. 31, 2006, U.S. Provisional Patent Application No. 60/763,357, dated Jan. 31, 2006, U.S. Provisional Patent Application No. 60/771,482, dated Feb. 9, 2006, U.S. Provisional Patent Application No. 60/771,484, dated Feb. 9, 2006, the contents of which are herein incorporated by reference in their entirety.

This application is related to the following concurrently filed commonly owned U.S. patent applications entitled, "Method And Apparatus For Generating A Technologist Quality Assurance Scorecard" (Ser. No. 11/699,348 filed Jan. 30, 2007); "Method And Apparatus For Generating A Patient Quality Assurance Scorecard" (Ser. No. 11/699,349 filed Jan. 30, 2007); "Method And Apparatus For Generating An Administrative Quality Assurance Scorecard" (Ser. No. 11/699,350 filed Jan. 30, 2007); and "Method And Apparatus For Generating A Clinician Quality Assurance Scorecard" (Ser. No. 11/699,351 filed Jan. 30, 2007), the contents of all of which are herein incorporated by reference in their entirety.

BACKGROUND OF THE INVENTION

1. Field of the Invention

The present invention relates to a quality assurance (QA) system and method that quantitatively rates users that perform and/or participate in medical procedures, particularly in the area of radiology. The present invention relates to systems, methods and computer-based software programs that analyze data and generate QA scorecards for radiologists. In the process of doing so, a number of objective data are collected for real-time and future analysis, thereby providing objective feedback to radiologists for continuing quality improvement. In the end, the invention is intended to improve patient safety and overall clinical outcomes.

2. Description of the Related Art

The first and foremost priority for any QA program is to improve quality of service. As QA programs are implemented in the medical field, the ultimate goal is to improve patient care. To accomplish this goal, products and/or services should offer procedures for increasing accountability and improving feedback among users that participate in a medical study. This ultimately will enhance patient diagnosis and/or treatment, which leads to objective improvements in overall health outcomes.

Medical imaging has undergone a transition from film-based imaging technologies to digital imaging technologies. Digital imaging technologies provide digital processing capabilities, such as image capture, image archive, image transfer, and image display that may be shared among users to the medical study. Digital imaging technologies further allow data that is associated with the digital processing operations to be captured and combined with the underlying digital imaging processing operations.

Accordingly, a need exists to leverage digital imaging technologies to increase accountability and improve feedback among users that participate in a medical study.

SUMMARY OF THE INVENTION

The present invention relates to systems, methods and computer-based software programs that provide a QA scorecard for users that participate in a radiology imaging study. The QA scorecard provides the framework for developing a comprehensive medical imaging QA program that defines objective benchmarks. One of ordinary skill in the art will readily recognize that this invention may be applied to other medical disciplines, as well as to non-medical disciplines.

According to one embodiment, the invention is directed to radiological-based medical studies using digital imaging technologies. The medical studies are performed by users that perform discrete tasks in an imaging study workflow sequence. According to one embodiment of the invention, users include clinicians, radiologists, technologists, administrators and patients, among other users. A typical workflow sequence includes imaging exam ordering, imaging exam scheduling, imaging exam acquisition, imaging exam processing, imaging exam archiving, imaging exam distribution, imaging exam display, imaging exam navigation, imaging exam interpretation, imaging exam reporting, communication and billing, among other sequences.

According to one embodiment of the invention, client computers, one or more servers, the imaging devices, one or more databases, and/or other components may be coupled via a wired media, a wireless media, or a combination of the foregoing to provided a unified data collection system.

According to one embodiment of the invention, the client computers may include any number of different types of client terminal devices, such as personal computers, laptops, smart terminals, personal digital assistants (PDAs), cell phones, portable processing devices that combine the functionality of one or more of the foregoing or other client terminal devices.

According to one embodiment, the client computer may include client computer agent modules that gather client computer monitoring data based on user actions that are performed. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer may include client computer agent modules that gather client computer monitoring data based on computer actions that are performed. According to one embodiment of the invention, the client computer agent modules also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment, the metrics module analyzes data that is associated with a defined list of quality assurance (QA) benchmarks to objectively evaluate radiologists, quantify a relative success of service delivery and provide educational (data-driven) feedback in order to optimize clinical performance, among other benefits. The QA metrics may be tied to economic incentives, such as a pay for performance (P4P) systems, to create financial rewards for those practitioners that provide high levels of quality-oriented service deliverables.

According to one embodiment, a quantifiable list of predefined performance parameters may be used by the program to measure overall performance of the radiologist, such as education, training, and research; diagnostic accuracy; clinician feedback; report content and structure; adherence to standards; timeliness of reporting; critical results reporting and communication; annotation of "key images"; complication rate and adverse outcomes, and/or other predetermined parameters.

According to one embodiment of the invention, performance metrics may be calculated by the program from various parameters, including completeness of data input, such as exam findings; utilization patterns, including economic outcomes, clinical outcomes, and/or medico-legal outcomes; a patient safety profile, such as requested use of ionizing radiation, contrast, invasive procedures; communication/reporting, including the availability of imaging data, the production of imaging data, and/or clinician consultations; timeliness, including time to review imaging results; feedback provided to the clinician and/or patient; participation in data collection and analysis, including outcomes analysis, reporting, and/or diagnostic accuracy; education and training, including imaging services and new technologies; peer review, including discretionary assessment of performance as it relates to imaging services and patient diagnosis/treatment, among other parameters.

According to one embodiment of the invention, the imaging devices may include any number of different types of imaging devices, such as magnetic resonance imaging (MRI) devices, computer tomograph (CT) imaging devices, angiograph imaging device, ultrasound imaging devices or other imaging devices.

According to one embodiment of the invention, the imaging devices may include, or be modified to include, imaging device agent modules. The imaging device agent modules may operate to provide data gathering and data exchange functionality. According to one embodiment, the invention may enable monitoring of actions that are performed on the imaging devices.

According to one embodiment of the invention, the imaging device agent modules may associate imaging device identifying information with actions that are performed on the imaging devices. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices.

According to one embodiment of the invention, databases or information sources include a Hospital Information System (HIS) 10, a Radiology Information System (RIS) 20, a Picture Archiving and Communication System (PACS) 30, an Electronic Medical Record (EMR), a patient specific imaging datasheet and/or other information sources.

According to one embodiment of the invention, the server may include a merging module that receives data from all devices that are networked to the server, including the client computers, the imaging devices, and/or databases or information sources. According to one embodiment of the invention, the received data may include at least client computer audit log data and/or image device audit log data. According to one embodiment, the merging module merges data that is captured during a medical examination, including user action data, client computer action data, imaging device action data, and other data.

According to one embodiment of the invention, the data that is collected during the imaging study may analyzed by a metrics module that performs prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module may automatically tally and record QA scores. The QA scores may be cross-referenced by the computer program to a number of independent variables including a technologist identifier, imaging modality, exam type, patient demographics, patient characteristics, patient body habitus, exposure parameters, image processing, exam location, equipment, day/time of exam for trending analysis, radiologist identification, referring clinician, clinical indication, among other variables.

According to one embodiment of the invention, a standard tag may be created by the program within the various informational sources to identify individual QA data parameters. The communication module may extract the parameters from the information sources to calculate metrics and generate a QA score for the radiologist.

According to one embodiment of the invention, the QA metrics module may analyze various parameters to calculate a QA score for the radiologist. According to one embodiment, the time-stamped data is a component part of objective data analysis. Imaging departments may utilize a program to record individual time-stamped data throughout the course of the imaging cycle, from the time an imaging exam is electronically ordered to the time the imaging report issued and reviewed. This is time-stamped data may be recorded into a QA database for subsequent analysis.

According to one embodiment, in order to optimize safety concerns and record/track cumulative data, the QA scorecard program provides patient safety data at any location where the patient is seeking and/or receiving medical imaging services. By storing the QA Scorecard data within a universal EMR, this data is made accessible to appropriate healthcare providers at any location.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
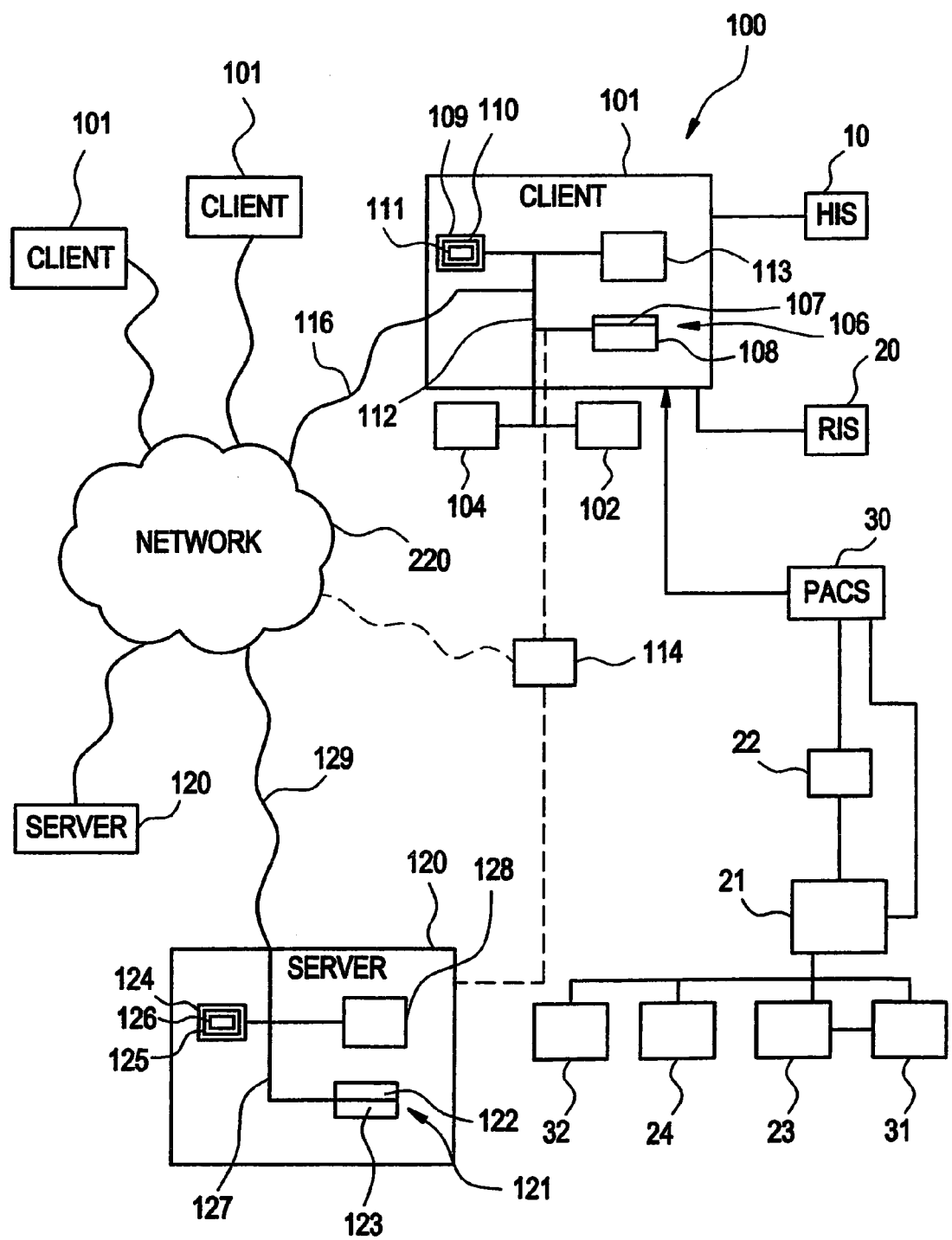
FIG. 1 illustrates a schematic diagram of a quality assurance scorecard system for radiology, according to one embodiment of the present invention.

The present invention relates to systems, methods, and computer-based software programs for generating quality assurance (QA) metrics, or scorecards, for radiologists that participate in radiological-based medical studies.

Radiological-based medical studies of the present invention are conducted using digital imaging technologies. The medical studies are performed by many users that perform discrete tasks in an imaging study workflow sequence. Typically, the workflow sequence is initiated by a clinician, such as a family practice physician, that examines a patient and orders an imaging examination. The clinician's staff contacts an imaging center and schedules the imaging examination. At the imaging center, a technologist operates one or more imaging devices to acquire patient images. In some cases, the number of patient images taken may total several hundred or several thousand images. During the image acquisition operation, the technologist may process the images, including applying algorithms to the raw imaging data in order to enhance selected image features, reconstructing the raw image data in different ways to optimize imaging views, and/or performing other image processing. Upon completion of the imaging examination, the patient may be discharged from the imaging facility and the images may be locally stored. Generally, imaging administrators periodically obtain the images from the local storage devices and archive the images in a database, such as a Picture Archival Retrieval System (PACS) and/or other imaging databases. The images may be archived and retrieved based on selected criteria, including patient name, patient reference number, patient identifier, physician identifier, and/or other selected criteria.

After the images are archived, the images may be distributed to one or more specialists, such as a radiologist. Alternatively, a message may be communicated to one or more specialists advising the specialists that the images are available and providing instructions for accessing the archived images from the PACS or other imaging databases. The radiologist may access the PACS or other imaging databases and may perform image display and image navigation functions. The radiologist interprets the images and may access decision support tools or other interpretation tools during the image interpretation process. Following the image interpretation, the radiologist may generate a report and/or otherwise communicate the image study results to the referring clinician, among others. Upon completion of the imaging process, the radiologist, an administrator, and/or other service provider may perform billing operations. Additionally, the administrator is tasked with defining the lines of responsibility for the participants of the imaging exam and for developing a comprehensive program that ensures appropriate levels of quality, while balancing economics, service deliverables and productivity. One of ordinary skill in the art will readily appreciate that the imaging study workflow sequence may include other operations.

According to one embodiment of the invention illustrated in FIG. 1, medical (radiological) applications may be implemented using the QA scorecard system 100. The QA scorecard system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, and/or other systems. The QA scorecard system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the QA scorecard system 100 of the present invention and the information systems, such the HIS 10, RIS 20, radiographic device 21, CR/DR plate reader 22, and (PACS) 30, etc., may be enabled to allow the QA scorecard system 100 to retrieve and/or provide information from/to these systems. According to one embodiment of the invention, standard tags may be created by the program 110 within the various informational sources to identify individual QA data parameters.

According to one embodiment of the invention, bi-directional communication between the QA scorecard system 100 of the present invention and the information systems allows the QA scorecard system 100 to update information that is stored on the information systems. According to one embodiment of the invention, bi-directional communication between the QA scorecard system 100 of the present invention and the information systems allows the QA scorecard system 100 to generate desired reports and/or other information.

The QA scorecard system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the QA scorecard system 100 may include separate programs 110 having code that performs desired operations. According to one embodiment of the invention, the program 110 that runs the QA scorecard system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, QA scorecard system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the above processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

Figure 2:
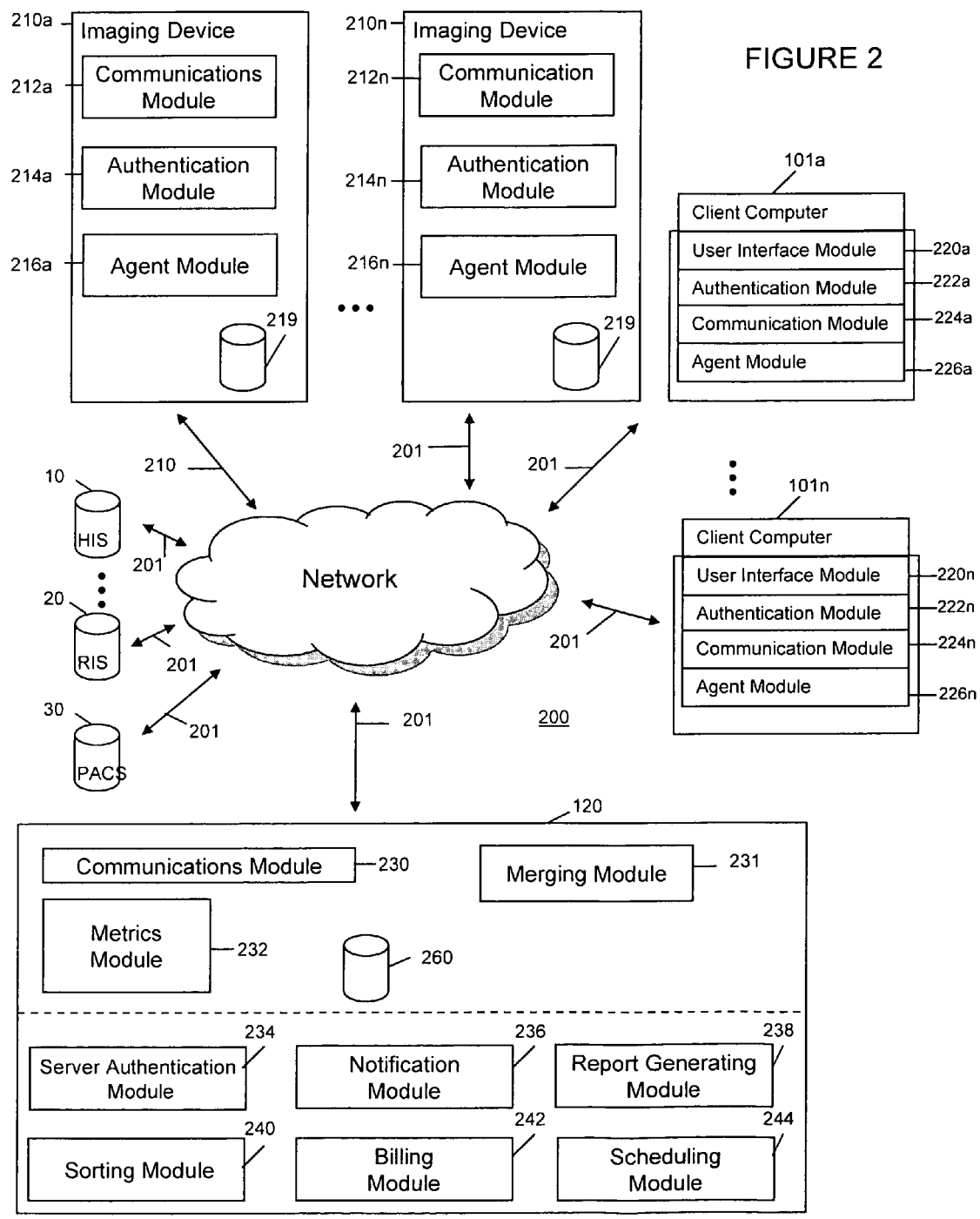
FIG. 2 illustrates a schematic diagram of a quality assurance scorecard system for radiology, according to another embodiment of the present invention.

FIG. 2 illustrates the QA scorecard system 100 for providing QA assessments of radiologists that access a radiology system, according to one embodiment of the invention. According to one embodiment, the client computers 101a-101n (hereinafter client computers 101), one or more servers 120, the imaging devices 210a-210n (hereinafter imaging devices 210), one or more databases (HIS 10, RIS 20, PACS 30, etc.), and/or other components may be coupled via a wired media, a wireless media, or a combination of the foregoing. According to one embodiment of the invention, the client computers 101, the server 120, the imaging devices 210, and the databases may reside in one or more networks, such as an internet, an intranet, or a combination thereof.

According to one embodiment of the invention, the client computers 101 may include any number of different types of client terminal devices, such as personal computers, laptops, smart terminals, personal digital assistants (PDAs), cell phones, portable processing devices that combine the functionality of one or more of the foregoing or other client terminal devices.

According to another embodiment of the invention, the client computer 101 may include several components, including processors, RAM, a USB interface, a telephone interface, microphones, speakers, a stylus, a computer mouse, a wide area network interface, local area network interfaces, hard disk drives, wireless communication interfaces, DVD/CD readers/burners, a keyboard, a flat touch-screen display, a computer display, and/or other components. According to yet another embodiment of the invention, client computers 101 may include, or be modified to include, software that may operate to provide data gathering and data exchange functionality.

According to one embodiment of the invention, the client computers 101, the servers 120, and/or the imaging devices 210 may include several modules. The modular construction facilitates adding, deleting, updating and/or amending modules therein and/or features within modules. The client computer 101 may include various modules, including a user interface module 220, an authentication module 222, a communications module 224, an agent module 226, and/or other modules. The servers 120 may include various modules, including a server communication module 230, a merging module 231, a metrics module 232, a server authentication module 234, a notification module 236, a report generating module 238, a sorting module 240, a billing module 242, a scheduling module 244, and/or other modules. The imaging devices 210 may include various modules, including a communications module 212, an authentication module 214, an agent module 216 and/or other modules, along with a local storage device 219. It should be readily understood that a greater or lesser number of modules might be used. One skilled in the art will readily appreciate that the invention may be implemented using individual modules, a single module that incorporates the features of two or more separately described modules, individual software programs, and/or a single software program.

According to one embodiment of the invention, the client computer 101 may communicate through a networking application. According to another embodiment, the user interface modules 220a-220n (hereinafter user interface modules 220) may support several interfaces including display screens, voice recognition systems, speakers, microphones, input buttons, and/or other interfaces. According to one embodiment of the invention, the user interface modules 220 may display the application on a user interface associated with the client computer 101. According to one embodiment of the invention, select functions may be implemented through the client computer 101 by positioning an indicator over selected icons and manipulating an input device 104, such as a stylus, a mouse, a keyboard, or other input devices.

With regard to user authentication, the authentication modules 222a-222n (hereinafter user authentication modules 222) may employ one of several different authentication schemes, as would be appreciated by those skilled in the art. According to one embodiment of the invention, the user authentication modules 222 may prompt users to input alpha-numeric code or other identifying information. According to another embodiment of the invention, the user authentication modules 222 may prompt users to provide biometric information (i.e., a thumbprint through a fingerprint scanner) or other suitable identifying information. If the user is not identified, then the user may be invited to resubmit the requested identification information or to take other action.

According to one embodiment of the invention, the client computers 101 may include communication modules 224a-224n (hereinafter communication modules 224) for enabling the client computers 101 to communicate with systems, including other client computers, the servers 120, the imaging devices 210, the databases and/or other systems. The client computers 101 may communicate via communications media 201 such as, for example, any wired and/or wireless media. Communications between the client computers 101, the imaging devices 210, the servers 120, and the databases may occur substantially in real-time, when the devices are coupled to the network. According to one embodiment of the invention, the communications module 224 may communicate with the servers 120 to exchange data, wherein the data exchange may occur with or without user awareness of the data exchange.

According to an alternative embodiment of the invention, communications may be delayed for an amount of time if, for example, one or more client computers 101, the server 120, the imaging devices 210, and/or the databases are not coupled to the network. According to one embodiment of the invention, any requests that are submitted while devices are not coupled to the network may be stored and propagated from/to the offline client computer 101, the databases and/or the imaging devices 210 when the target devices are re-coupled to the network. One of ordinary skill in the art will appreciate that communications may be conducted in various ways and among various devices.

According to one embodiment of the invention, user authentication information and/or identification information may be forwarded to the servers 120 to perform various functions. According to another embodiment of the invention, the servers 120 may operate to coordinate communications between the applications that are associated with the client computers 101, the imaging devices 210, and/or the databases.

According to one embodiment of the invention, the client computers 101 may include, or be modified to include, client computer agent modules 226a-226n (hereinafter client computer agent modules 226). The client computer agent modules 226 may operate to provide data gathering and data exchange functionality. According to one embodiment, the invention may enable monitoring of actions that are performed on the client computers 101.

According to one embodiment of the invention, the client computer agent modules 226 may associate client computer identifying information with actions that are performed on the corresponding client computers 101. According to one embodiment of the invention, data monitoring features may be employed to generate client computer audit logs. According to one embodiment of the invention, client computer audit logs may be produced to reconstruct actions, such as user actions, computer actions, and/or other actions that are performed on (or by) the client computers 101.

According to one embodiment, the client computer agent modules 226 may gather client computer monitoring data based on user actions performed, such as user login information; data files and databases that are accessed; information that is requested, including patient names/identifiers, exam results; information that is retrieved; client computer access information, including user information, time of access, time of exit, etc.; the application(s) that are used; information that is obtained from the server 120, including time of access, patient identifiers, volume of data retrieved, etc.; information that is obtained from the imaging devices 210, including time of access, patient identifiers, volume of data retrieved, etc.; information that is processed at the client computer 101, including time stamp information; and other user action data. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer agent modules 226 may gather client computer monitoring data based on computer actions performed, such as when data is exchanged; the type of input device used; whether reports are printed; when data is saved; an Internet Protocol (IP) address of devices that are communicated with; a location of data storage/retrieval; etc.; and/or other computer action data. According to one embodiment of the invention, the imaging device agent modules 216 also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment of the invention, the server 120 may include a server authentication module 234 that receives authentication information that is entered into a corresponding client computer 101 via the authentication modules 222. The server authentication module 234 may compare the identifying information with existing records and operate as a gatekeeper to the QA scorecard system 100. If the user is determined to be a registered user, the authentication module 234 may attempt to authenticate the registered user by matching the entered authentication information with access information that exists on the servers 120. If the user is not authenticated, then the user may be invited to resubmit the requested identifying information or take other action. If the user is authenticated, then the servers 120 may perform other processing. For example, the client computers 101 may receive information from the servers 120 and/or from another authenticated client computers.

According to one embodiment of the invention, the imaging devices 210 may include any number of different types of imaging devices, such as magnetic resonance imaging (MRI) devices, computer tomograph (CT) imaging devices, angiograph imaging device, ultrasound imaging devices or other imaging devices. According to another embodiment of the invention, the imaging devices 210 may include several components such as processors, databases 219a-219n (hereinafter databases 219), RAM, a USB interface, a telephone interface, microphones, speakers, a stylus, a computer mouse, a wide area network interface, local area network interfaces, hard disk drives, wireless communication interfaces, a keyboard, a flat touch-screen display, a computer display, and/or other components.

According to one embodiment of the invention, the imaging devices 210 may include, or be modified to include, imaging device agent modules 216a-216n (hereinafter imaging device agent modules 216). The imaging device agent modules 216 may operate to provide data gathering and data exchange functionality. According to one embodiment, the invention may enable monitoring of actions that are performed on the imaging devices 210.

According to one embodiment of the invention, the imaging device agent modules 216 may associate imaging device identifying information with actions that are performed on the imaging devices 210. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices 210.

According to one embodiment, the imaging device agent modules 216 may gather image device monitoring data based on user actions performed, such as user login information; imaging modalities; parameters that are selected to perform the imaging modalities, including motion information, positioning information, exposure information, artifact information, collimation information; number of times an imaging exam is performed; data files and databases that are accessed; information that is requested, including patient names/identifiers; information that is retrieved; imaging device access information, including user information, time of access, time of exit, etc.; information that is stored to the server 120, including time of storage, patient identifiers, volume of data stored, etc.; information that was obtained from the imaging devices 210, including time of access, patient identifiers, volume of data stored, etc.; information that was processed at the imaging device 210, including time stamp information; and other user action data.

According to one embodiment, the imaging device agent modules 216 may gather imaging device monitoring data based on imaging device actions performed, such as when data is exchanged; the type of input device used; whether reports are printed; when data was saved; an Internet Protocol (IP) address of devices that were communicated with; a location of data storage/retrieval; imaging device parameter adjustments; and other imaging device data. According to one embodiment of the invention, the imaging device agent modules 216 also may gather imaging device specification data, such as resolution data, IP address data, processing speed data, and other imaging device specification data. According to one embodiment of the invention, the imaging device monitoring data and/or imaging device specification data may be stored in database 219. According to one embodiment of the invention, the imaging device monitoring data and/or imaging device specification data of the program 110 may be provided in real-time. According to another embodiment of the invention, the imaging device monitoring data and/or imaging device specification of the program 110 may be employed to calculate user QA metrics. The inventor has previously submitted an application describing an apparatus for automating QA in medical imaging, as described in U.S.

patent application Ser. No. 11/412,884 filed on Apr. 28, 2006, the entire contents of which are hereby incorporated by reference.

According to one embodiment of the invention, the server 120 may include a merging module 231 that receives data from all devices that are networked to the server 120, including the client computers 101, the imaging devices 210, and/or databases. According to one embodiment of the invention, the received data may include at least client computer audit log data and/or image device audit log data. The merging module 231 may locally store the received data in a storage device 260 and/or may store the received data in an external storage device. The merging module 231 merges data that is captured during a medical examination, including user action data, client computer action data, imaging device action data, and other data.

According to one embodiment of the invention, the server 120 may include a sorting module 240 that enables sorting of the data, including the merged data. According to one embodiment of the invention, the sorting module 240 may sort the data based on various sorting criteria, including the chronology of data receipt, the type of device that originated the data, the type of technology used to obtain the data (e.g. CT, MRI, sonogram, etc.), the type of institution in which a data was obtained, the type of professional that obtained the data (i.e., radiologist, technologist, etc.), the user that is associated with the data, the patient that is associated with the data, demographic information, patient population information, the workflow sequence in which the data was captured, the severity of exam results, and/or other sorting criteria. According to one embodiment of the invention, the sorted data may enable tracking, reconstruction, reporting and/or monitoring of actions that are performed during medical examinations. According to one embodiment of the invention, the criteria associated with medical examinations may be used by the program to calculate QA scorecard metrics.

According to one embodiment of the invention, the server 120 may include a communications module 230 that communicates with the client computer 101, imaging devices 210 and/or databases to obtain information regarding the status of the imaging study along a defined workflow sequence. According to one embodiment of the invention, a defined workflow sequence includes various operations, such as image exam ordering, image exam scheduling, image exam acquisition, image processing, image archiving, image navigation, image interpretation, image exam reporting, image exam communication, and/or image exam billing. According to one embodiment of the invention, the communications module 230 provides the status of the imaging study workflow sequence including identifying the current user that is responsible for the image study, a completion percentage of the current stage of the imaging study, and/or other status information. According to one embodiment of the invention, the status of the imaging study workflow may be communicated to users in real-time and/or stored. According to one embodiment of the invention, parameters may be derived from the status of the imaging study workflow sequence by the program 110 to generate a QA scorecard for the various users.

According to one embodiment of the invention, the server 120 may include a report generating module 238 that generates reports based on the occurrence of pre-defined events, including a periodic query of the status of the imaging study, an interpretation that is forwarded by the radiologist, a clinical finding that is submitted by the clinician, and/or the occurrence of other pre-defined events.

According to one embodiment of the invention, the server 120 may include a billing module 242. According to one embodiment, the billing module 242 performs billing functions following completion of the reporting/communication process. The billing module 242 may analyze metrics to assess operational efficiency and accuracy of charges billed and to calculate any additional expenses that occur due to limitations in reporting by users, such as radiologists. According to one embodiment, the additional expenses may take a number of forms and may result from uncertainty and equivocation within the radiology report or radiologist recommendations for additional imaging exams, consultations, and procedures (e.g. biopsy). The billing module 242 may correlate imaging costs with quality of service deliverables, such as diagnostic accuracy and clinical outcomes.

According to one embodiment of the invention, the server 120 may include a scheduling module 244 that enables electronic scheduling, including image exam scheduling. According to one embodiment, the scheduling module 244 may include bi-directional electronic scheduling that provides real-time tracking features to update parties of scheduling changes. The scheduling module 244 may communicate with the communication module 230 and/or notification module 236, among other modules, to communicate the status of an appointment to users in real-time and/or stored.

According to one embodiment of the invention, the server 120 may include a notification module 236 that generates notifications and/or alerts based on the completion of reports, scheduling or the occurrence of predefined events. The notifications may be triggered by the release of items, such as status information, completion of an imaging report, change of an appointment, and/or other items. The notification module 236 may include monitoring features and/or confirmation features that track and record events, including the date and time that a notification is sent, the date and time that a notification is delivered, the date and time that a notification is opened, such as by return of an acknowledge receipt message, among other events. According to one embodiment, the notification module 236 may generate and forward notifications and/or alerts to client computers 101 and/or mobile devices, using known communication techniques including electronic mail messages, voice messages, telephone messages, text messages, instant messages, facsimile, and/or other communication techniques.

According to one embodiment of the invention, variables that are determined to have a deficiency during the imaging study process and that exceed a pre-determined QA standard threshold may trigger the computer program 110 to produce a notification and/or alert through the notification module 236 that may be instantaneously sent to users, via one or more communications techniques, alerting users as to the specific type of deficiency and requirement for correction.

According to one embodiment of the invention, a minimal amount of the data that is processed at the servers 120 may be stored in storage device 260 by the program 110. In other words, the servers 120 may perform data gathering and/or document generating functions and may thereafter purge all or portions of the retrieved data according to specified criteria. As a result, according to one embodiment, the program 110 may minimize security risks associated with exposing any confidential medical records to unauthorized parties at the servers 120. According to another embodiment of the invention, the retrieved data may be stored at the servers 120 by the program 110 for a predetermined amount of time before being purged. According to yet another embodiment of the invention, public record information, non-confidential retrieved data, and/or tracking information, such as client computer log files and/or image device log files may be stored in storage device 260 by the program 110.

According to one embodiment of the invention, the metrics module 232 may receive objective scores, such as a Likert scale of 1-4, to quantify user performance. For example, a score of 1 may be considered "non-diagnostic". This means little or no clinically useful (diagnostic) information is contained within the image study. Since the available information obtained during the examination of the patient does not answer the primary clinical question (i.e., indication for the study), then by definition this requires that the imaging exam be repeated for appropriate diagnosis.

A score of 2 may be considered "limited". This means that the information obtained during the image study is less than expected for a typical examination of this type. However, the information contained within the image study is sufficient to answer the primary clinical question. A requirement that this exam be repeated is not absolute, but is preferred, in order to garner maximal diagnostic value.

A score of 3 may be considered "diagnostic". This means that the information obtained during the image study is representative of the broad spectrum of comparable images, allowing for the patient's clinical status and compliance. Both the primary clinical question posed, as well as ancillary information, can be garnered from the image for appropriate diagnosis.

A score of 4 may be considered "exemplary". This means that the information obtained during the image study and overall image quality serves as an example that should be emulated as the "ideal" for that specific imaging study and patient population.

According to one embodiment of the invention, the data that is collected during the imaging study may analyzed by a metrics module 232 for performing prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module 232 may automatically tally and record QA scores in a selected database. The QA scores may be cross-referenced by the computer program 110 to a number of independent variables including a technologist identifier, imaging modality, exam type, patient demographics, patient characteristics, patient body habitus, exposure parameters, image processing, exam location, equipment, day/time of exam for trending analysis, radiologist identification, referring clinician, clinical indication, among other variables. According to one embodiment of the invention, the report generating module 238 may access the QA scores to display results from the metrics module 232. The reports may be accesses at any time by users, including the clinician, the radiologist, the technologist, and/or the department/hospital administrator to review individual and collective performance results. The trending analysis provided by this data can in turn be used for educational purposes, performance review, and new technology deployment.

According to one embodiment, the metrics module 232 analyzes data that is associated with a defined list of quality assurance (QA) benchmarks to objectively evaluate radiologists, quantify a relative success of service delivery and provide educational (data-driven) feedback in order to optimize clinical performance, among other benefits. The QA metrics may be tied to economic incentives, such as a pay for performance (P4P) systems, to create financial rewards for those practitioners that provide high levels of quality-oriented service deliverables.

According to one embodiment, a quantifiable list of predefined performance parameters may be used by the program 110 to measure overall performance of the radiologist, such as education, training, and research; diagnostic accuracy; clinician feedback; report content and structure; adherence to standards; timeliness of reporting; critical results reporting and communication; annotation of "key images"; complication rate and adverse outcomes, and/or other predetermined parameters. According to one embodiment of the invention, performance metrics may be calculated by the program 110 from various parameters, including completeness of data input, such as exam findings; utilization patterns, including economic outcomes, clinical outcomes, and/or medico-legal outcomes; a patient safety profile, such as requested use of ionizing radiation, contrast, invasive procedures; communication/reporting, including the availability of imaging data, the production of imaging data, and/or clinician consultations; timeliness, including time to review imaging results; feedback provided to the clinician and/or patient; participation in data collection and analysis, including outcomes analysis, reporting, and/or diagnostic accuracy; education and training, including imaging services and new technologies; peer review, including discretionary assessment of performance as it relates to imaging services and patient diagnosis/treatment, among other parameters.

According to one embodiment of the invention, the predefined parameters (see the Table below) may be used to calculate an individual radiologist QA score. The QA score may be used as a multiplier for technical reimbursement or salary. According to one embodiment of the invention, higher priority variables, such as diagnostic accuracy and critical results reporting, may provide the highest multipliers, when compared with lower priority variables, such as education & training, annotation of key images. According to one embodiment of the invention, each variable may be assigned a scoring scale of 1-10. According to one embodiment of the invention, the QA score may provide a method to standardize and track technologist QA profiles on local, national, and international levels. For example, a positive QA score of +18, may equate to a reimbursement fee of 118%, while a negative QA score of −14 would equate to a reimbursement rate of 86% of the standard fee. According to one embodiment, the distribution profile for the collective group may be a normalized to a bell-shaped curve, thereby maintaining no net increase or decrease in overall payments by third party payers.

TABLE

| Quantifiable Parameters | Scoring System | Source of Data |
|---|---|---|
| Education & Training | −1 … +1 | Departmental/Institutional Databases |
| Diagnostic Accuracy | −10 … +10 | EMR, NLP |
| Clinician Feedback | −3 … +3 | Computerized Surveys |
| Report Content & Structure | −2 … +2 | RIS |
| Adherence to Standards | −2 … +2 | Professional Guidelines |
| Report Timeliness | −2 … +2 | RIS |
| Critical Results & Communication | −5 … +5 | RIS, PACS |
| Annotation of Key Images | −1 … +1 | PACS |
| Complication Rate | −4 … +4 | Departmental/Institutional Databases |

According to one embodiment of the invention, communication and reporting parameters may include, time from imaging data receipt to report completion; time from report completion to receipt by clinician; radiologist time reviewing imaging data, such as imaging data open time and imaging data close time; radiologist time components for individual imaging exam segments; perceived clinician value for report; report structure; report content; report organization; imaging links, including complete imaging file, key images, snapshot; ancillary data, including teaching files, NLM, review articles; communication; method of communication; acknowledgement of receipt of communication; bi-directional consultation; time to initiate treatment; tracking of follow-up recommendations; clinician satisfaction; subjective value; referral patterns; among other parameters.

According to one embodiment of the invention, the communication module 230 may access a number of informational sources, including the electronic medical record (EMR); the computerized physician order entry system (CPOE); the hospital information systems (HIS) 10, the radiology information systems 20 (RIS); the picture archival and communication system (PACS) 30; subjective feedback from the radiologist, patient, and clinician peer group; and/or other informational sources, to obtain clinical performance parameters. According to one embodiment, standard tags may be created within the various informational sources to identify individual QA data parameters.

Figure 3A:
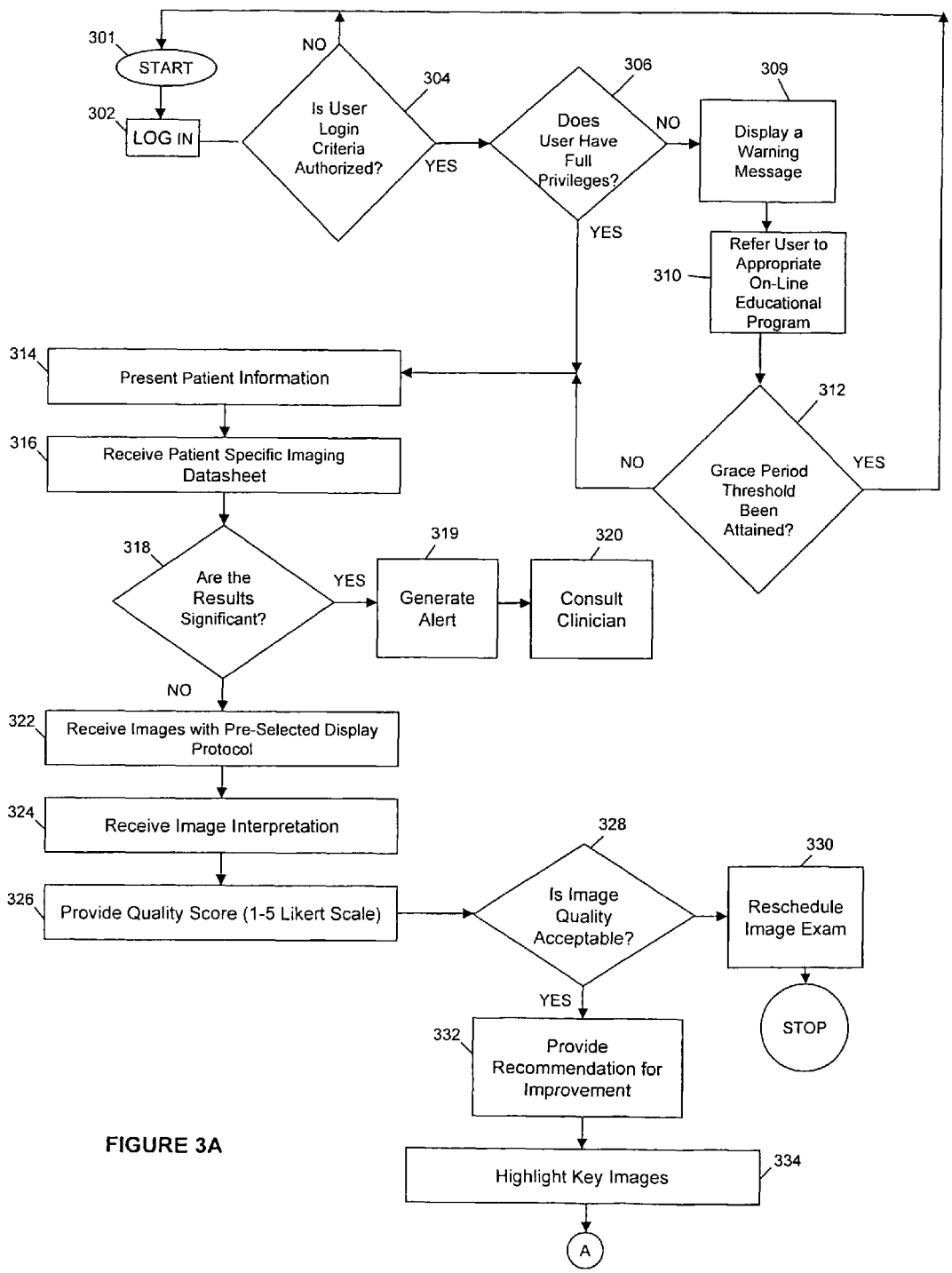
FIGS. 3A and 3B illustrate a flow chart of a workflow sequence quality assurance program for image interpretation from the perspective of a radiologist, according to one embodiment of the present invention.
Figure 3B:
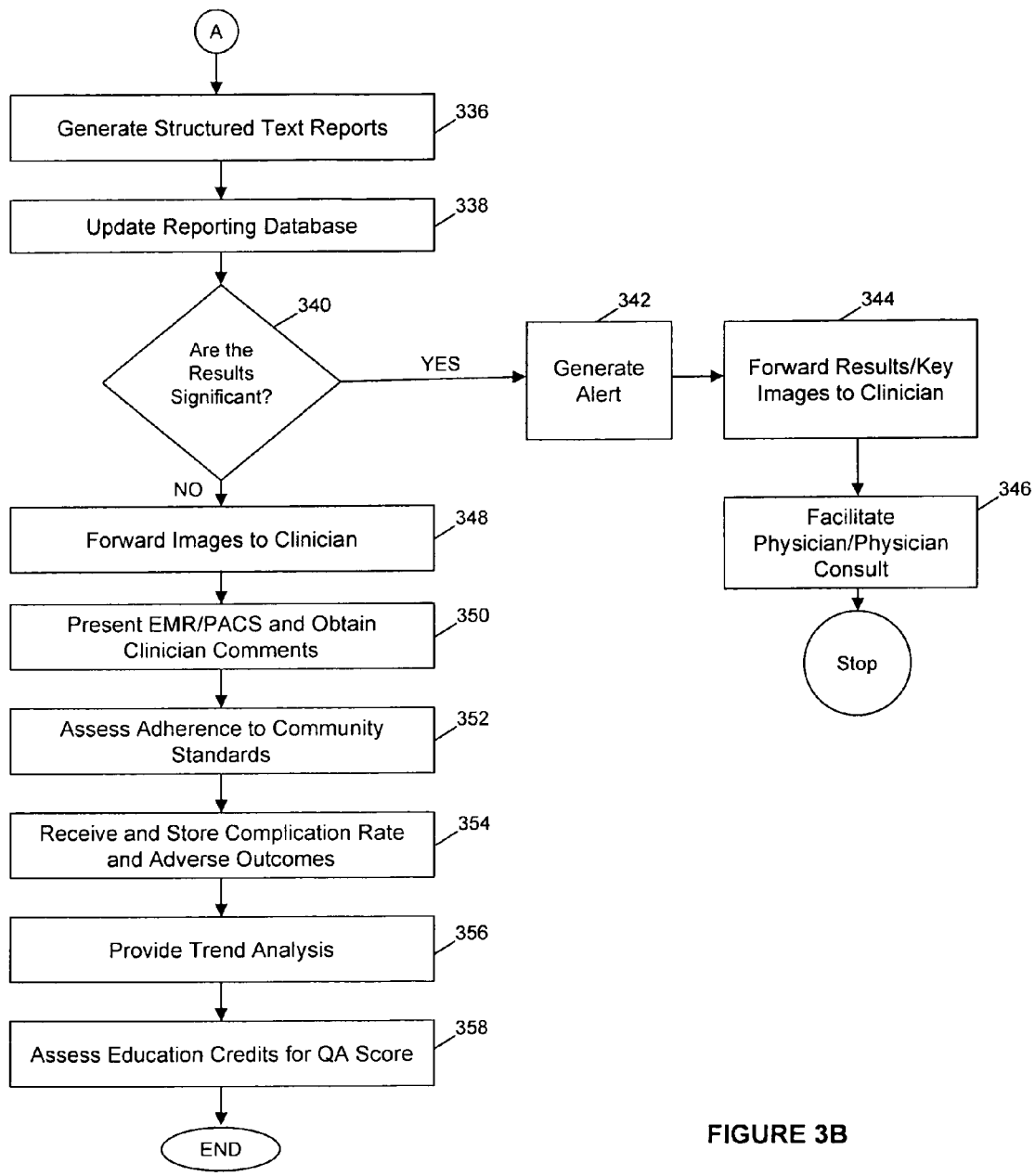

According to one embodiment of the invention illustrated in FIGS. 3A and 3B, the QA scorecard program 110 presents a welcome screen in operation, or step, 301. In operation 302, the QA scorecard program 110 displays a log-in screen and receives log-in criteria, such as a username and password. In operation 304, the QA scorecard program 110 compares the user log-in criteria against pre-stored log-in criteria for authorized users to determine if the user may gain access to the system. If the user log-in criteria is not approved, then the QA scorecard program 110 may notify the user of the registration failure and may return to the main log-in screen. If the user log-in criteria is approved, then in operation 306, the QA scorecard program 110 may determine whether or not the user is assigned full privileges to perform actions within the QA scorecard program 110. If the user has full privileges, then the QA scorecard program 110 requests patient information or a patient identification number in operation 314.

According to one embodiment of the invention, a reduction of privileges may be prescribed for various predefined reasons, including failure to follow a predefined protocol, frequently misdiagnosing an ailment, failure to follow a cost effective treatment plan, and/or failure to complete continuing medical education (CME) credits, among other predefined reasons.

According to one embodiment of the invention, if the user does not have full privileges, then in operation 309, the QA scorecard program 110 displays a warning message on the user interface advising the user that less than full privileges are associated with the log-in criteria. In operation 310 the QA scorecard program 110 may identify and recommend re-credentialing programs, including approved CME courses, computer training, or other re-credentialing programs. The QA scorecard program 110 will enable the user to immediately access the recommended re-credentialing programs through the QA scorecard program 110. According to one embodiment, the user may defer starting the recommended re-credentialing programs until a future date. After users successfully complete the re-credentialing program, the QA scorecard program 110 may restore full privileges to the user.

According to one embodiment of the invention, policies governing removal and re-institution of imaging privileges may be under the jurisdiction of a multi-disciplinary QA team including radiologists, administrators, and chief technologists, who would all have input into the overall process of reviewing data from the CPOE system.

According to one embodiment of the invention, the warning message displayed in operation 309 also may identify a grace period that is granted for regaining full privileges before all the privileges are revoked. According to one embodiment of the invention, the grace period may be defined by a threshold, such as a number of log-ins, a number of days, or other threshold that may not be exceeded before all privileges are revoked.

According to one embodiment of the invention, the grace period threshold may be determined by the program 110 based on predetermined factors, such as the frequency of occurrence of one of predefined triggers, the severity of a error, the amount of time required to complete a re-credentialing program, and/or other factors. In operation 312, the QA scorecard program 110 may determine if the user has exceeded the allowed number of grace period log-ins. If the number of allowed grace period log-ins are exceeded, then the QA scorecard program 110 may revoke all privileges and the user may be presented with an alert that all privileges are revoked. The QA scorecard program 110 may prevent the user from proceeding further in the QA scorecard program 110 and the QA scorecard program 110 may return to the welcome screen. The QA scorecard program 110 may provide the user with contact information for re-establishing privileges.

If the grace period threshold has not been exceeded, then the QA scorecard program 110 receives patient information or a patient identification number in operation 314. According to one embodiment of the invention, the QA scorecard program 110 accesses one or more information sources, including the electronic medical record (EMR), the hospital information system 10 (HIS), the radiology information system 20 (RIS), the PACS 30, among other information sources to obtain information and/or records associated with the selected patient.

In operation 316, the QA scorecard program 110 displays the imaging data sheet that is customized by a user for the patient. According to one embodiments of the invention, the imaging data sheet provides users with important aspects of the patients medical history. The imaging data sheet may have a standard format and include data, such as past medical and surgical history; prior imaging exams and results, including those performed at outside facilities; current clinical problems; pertinent findings on physical exam; pertinent laboratory and/or pathology data; ancillary data, including procedural findings (e.g. colonoscopy, bronchoscopy), operative or consultation notes, clinical testing (e.g., EEG, EKG); technical information related to the imaging exam performed; technologist observations, including pertinent findings and measurements; technologist notes, including complications, exam limitations; among other data. The QA scorecard program 110 facilitates creation of a universal, patient-specific imaging data sheet for digital images that could be stored in the EMR, RIS, and/or PACS, among other information systems.

According to one embodiment of the invention, the imaging data sheet may include all pertinent clinical data elements that are related to the diagnosis being evaluated. According to one embodiment of the invention, the data elements include past medical and surgical history; allergies, with particular emphasis directed to contrast media used in medical imaging;

risk factors, including family history and tumor markers; non-imaging data, including laboratory, clinical testing, pathology; clinical indication and presumptive diagnosis, which prompted the ordered imaging exam; findings on physical examination; historical imaging data, including outside imaging exams and findings; and/or other data elements.

According to one embodiment of the invention, each time a new entry or modification is made to the imaging data sheet, a time-stamp may be included in the record by the program 110, along with the identification of the person inputting (or modifying) the data. According to one embodiment of the invention, each user may create profiles for the imaging data sheet and may customize the imaging data sheet display to their own individual preferences. According to one embodiment of the invention, the customized imaging data sheet may be linked by the program 110 to users via a log-in criteria.

According to one embodiment of the invention, new data may be input into the imaging data sheet via the QA scorecard program 110 by clinicians, nurses, radiologist, technologist or other authorized users. According to one embodiment of the invention, new data may be input into the imaging data sheet via the QA scorecard program 110 through computer-derived entry using natural language processing (NLP). According to one embodiment of the invention, the imaging data sheet may have separate tabs for each individual imaging modality, and may store technical data, measurements, and technologist notes specific to each individual exam/modality.

According to one embodiment of the invention, the radiologist may review the data elements that are entered into the CPOE system. The availability of the data elements provides an opportunity for the technologist and/or radiologist to clarify any discrepancies or clinical questions. According to one embodiment of the invention, discrepancies are defined to include data that is inconsistent with other information that is included in the record. For example, the clinician may input data indicating that no prior history of cancer exists. However, a prior imaging report may show past medical history of cancer.

In operation 318, the radiologist makes an initial determination and provides the QA scorecard program 110 with an indication of whether or not the results are significant. If the QA scorecard program 110 receives information of clinically unexpected or emergent findings by the radiologist during the course of imaging exam interpretation, the QA scorecard program 110 generates an alert in operation 319 that notifies the ordering clinician to immediately contact the radiologist to establish a consultation between the radiologist and the clinician in operation 320.

According to one embodiment of the invention, the critical results reporting/communication process may be automated. According to one embodiment of the invention, users may create an automated communication pathway for critical results, which may be customized to the preferences of each user. For example, a clinician may select to have critical/unexpected results communicated by the program 110 via e-mail, while another use may select to have critical/unexpected results communicated to via text paging. According to one embodiment of the invention, the communication may be recorded and an electronic audit trail may be established documenting the date, time, and information conveyed.

According to one embodiment of the invention, whether the communication occurs electronically or verbally, the QA scorecard program 110 documents the communication by time stamping and storing the communication for future analysis. Upon receipt of the alert, the clinician may immediately contact the imaging department staff (i.e. radiologists, technologists, administrators) to discuss the clinical concerns. Any delays that are introduced by the radiologist in generating imaging reports may translate into delays by clinicians in diagnosing and establishing a treatment plan. Upon receiving timely imaging reports, the clinician may contact the patient to advise of the results. The QA scorecard program 110 documents communications between the clinician and patient by time stamping and storing the communication for future analysis. According to one embodiment, timeliness of reporting may be included in the radiologist QA scorecard metrics.

According to one embodiment of the invention, the QA scorecard program 110 may record time stamps for various steps in the imaging process, including the time the imaging exam is scheduled; the time of patient arrival; the time that the imaging exam is started and completed; the time that the imaging exam is transmitted to PACS for radiologist interpretation; the time the radiologist opens the imaging exam; the time that the imaging exam is closed; the time that the report is dictated; and the time that the imaging report is signed. According to one embodiment of the invention, QA scorecard parameters for reporting and communication may include criteria such as, time from image receipt to receipt by clinician; time from image receipt to actual review; specific components of the image reviewed by radiologist; radiologist time reviewing imaging data, such as image open time and image close time; clinician time components for responding to alert; method of communication; acknowledgement of receipt of communication; bi-directional consultation; time to initiate treatment; tracking of follow-up recommendations; clinician satisfaction; subjective value; referral patterns; among other criteria. Using these measurements, the QA scorecard program 110 may derive reporting times and may automatically record the reporting time in the QA database, among other information sources.

According to one embodiment, the time-stamped data is an integral part of objective data analysis. Imaging departments are able to utilize the program 110 to record individual time-stamped data points throughout the course of the imaging cycle, from the time an imaging exam is electronically ordered to the time the alert is issued and acknowledged. After the image alert is received, time-stamped data may be tracked by the program 110 within the EMR, which records clinician actions, in the form of recording progress notes, consultations, and the ordering of clinical tests, imaging studies, and various treatment options (e.g. drug therapy). In either case, the QA scorecard program 110 enables the clinician to enter data electronically into the EMR. This time-stamped data may be recorded into a QA database for subsequent analysis by the program 110. One such analysis may include an assessment of the time incurred between the imaging exam and initiation of clinical treatment.

When the imaging study does not include unexpected results or emergent findings, the QA scorecard program 110 presents images to the radiologist with pre-selected display protocol in operation 322.

In operation 324, the QA scorecard program 110 presents the imaging study to the radiologist and receives an image interpretation from the radiologist. The QA scorecard program 110 enables the radiologists to dynamically manipulate the medical images. The QA scorecard program 110 may access PACS and MPR workstations to enable radiologists to reconstruct images in multiple imaging planes, perform image processing, and use a variety of workstation tools to highlight potential areas of pathology.

In operation 326, the QA scorecard program 110 enables the radiologist to rate the image quality of the various images that form the imaging study. In operation 328, the QA scorecard program 110 enables radiologist to identify whether the image quality is acceptable for review.

If the image quality is non-diagnostic, the QA scorecard program 110 may request that the imaging exam be rescheduled in operation 330. If the image quality is poor, but diagnostic, then the QA scorecard program 110 enables the radiologist to provide recommendation to the technologist in operation 332 for improving future imaging studies having similar parameters. According to one embodiment, recommendations may include producing alternate image examinations, adjusting dosage or providing other guidance. If the image quality is good and diagnostic, then the QA scorecard program 110 enables the radiologist to provide comments of encouragement to the technologist in operation 332 for improvement.

According to one embodiment of the invention, the QA scorecard program 110 presents the radiologist with an automated pop-up window to evaluate image quality using a scoring method, such as the Likert scale. According to one embodiment of the invention, the QA scorecard program 110 may also enable the radiologist to include an optional problem list to provide detailed comments regarding image quality. According to one embodiment, these image quality evaluations may be automatically entered by the program 110 into an electronic database and may be communicated to the metrics module 232. According to one embodiment, the image quality evaluations may be included in QA trending analysis by the program 110. The QA scorecard program 110 allows the radiologist to provide feedback regarding image quality without needing to open alternate applications.

In operation 334, the QA scorecard program 110 enables the radiologist to highlight key images from a large data set. As imaging datasets increase in size and complexity with an exponential increase in the number of CT images contained in a single exam, it is overwhelming and time consuming for a clinician to attempt to navigate and review the entire dataset. Furthermore, the large memory requirements of datasets, which can exceed 500 MB, may consume network bandwidth and cause delays in data access. According to one embodiment, the QA scorecard program 110 may enable the radiologists to identify selected subset of images with pertinent findings. According to one embodiment, the QA scorecard program 110 may enable the radiologist to create a small imaging subset of "key images," that may be highlighted and may include annotations in the areas of pathology. According to one embodiment, the QA scorecard program 110 may generate "key image" folders that enable quick and easy review of the dataset. According to one embodiment, the QA scorecard program 110 may enable the "key image" folders to be presented for patient education, quick and reliable comparison with historical exam, and application of decision support tools to automated quantifiable measurements, among other benefits. According to one embodiment of the invention, the annotation of "key images" may be used to calculate QA scorecard metrics.

In operation 336, the QA scorecard program 110 enables the radiologist to generate a structured text report that may be correlated with the imaging study. According to one embodiment, structured text reports use a standardized lexicon that enable large scale database mining of reports to establish community and nationwide norms. According to one embodiment, reporting templates utilize the same data elements to create consistent and reproducible data that is used to perform statistical analysis. According to one embodiment, the QA scorecard program 110 may perform the statistical analysis on a continual basis and may store the results in the QA database.

In operation 338, the QA scorecard program 110 may update patient's data profile in the HIS 10, RIS 20, EMR or other information source to include marked-up images, the structured text report and other documents that are generated by the radiologist.

In operation 340, after the radiologist has interpreted the imaging study, the QA scorecard program 110 prompts the radiologist to provide a determination of whether or not the imaging results are significant. If the QA scorecard program 110 receives an indication of clinically unexpected or emergent findings, the QA scorecard program 110 generates an alert in operation 342 that notifies the ordering clinician to immediately contact the radiologist to directly receive these emergent findings. In operation 344, the QA scorecard program 110 may forward the imaging results and/or key image results to the clinician for review.

Whether the communication occurs electronically or verbally, the QA scorecard program 110 documents the communication by time stamping and storing the communication for future analysis. Upon receipt of the alert, the clinician may immediately contacts the imaging department staff (i.e. radiologists, technologists, administrators) to discuss the clinical concerns in operation 346. The clinician may contact the patient to advise of the results. The QA scorecard program 110 documents the communication between the clinician, patient, and/or radiologist by time stamping and storing the communication for future analysis.

According to one embodiment of the invention, QA scorecard parameters for reporting and communication may include criteria such as, time from image receipt to receipt by clinician; time from image receipt to actual review; specific components of the image reviewed by radiologist; radiologist time reviewing imaging data, such as image open time and image close time; clinician time components for responding to alert; method of communication; acknowledgement of receipt of communication; bi-directional consultation; time to initiate treatment; tracking of follow-up recommendations; clinician satisfaction; subjective value; referral patterns; among other criteria.

According to one embodiment, the time-stamped data is a part of objective data analysis. Imaging departments are able to record individual time-stamped data points throughout the course of the imaging cycle, from the time an imaging exam is electronically ordered to the time the alert is issued and acknowledged. After the image alert is received, time-stamped data may be tracked within the EMR, which records clinician actions, in the form of recording progress notes, consultations, and the ordering of clinical tests, imaging studies, and various treatment options (e.g. drug therapy). In either case, the QA scorecard program 110 enables the clinician to enter data electronically into the EMR. This is time-stamped data may be recorded into a QA database for subsequent analysis. One such analysis may include an assessment of the time incurred between the imaging exam and initiation of clinical treatment.

When the imaging study does not include unexpected results or emergent findings, the QA scorecard program 110 presents imaging study and/or key images to the clinician in operation 348. According to one embodiment, the QA scorecard program 110 may present pop-up menus to the clinician upon access of a medical imaging exam and/or imaging report. According to one embodiment, the pop-up menu may present questions and may prompt the clinician to respond using the Likert scale, among other methods. According to one embodiment, the questions may include was the radiological diagnosis consistent with the patient's presumptive clinical diagnosis and supporting clinical data?; was the information contained within the report understandable and presented in a clear and logical fashion?; were appropriate clinical significance and follow-up recommendations provided in the report to guide further clinical action?; among other questions. According to one embodiment of the invention, the answers may be used to calculate radiologist QA scorecard metrics.

According to one embodiment, responses to the above questions may identify each clinician's inherent biases, based on a clinician's answer profile. The responses may be statistically adjusted by the program 110 to normalize the impact on the QA score. For example, if one clinician consistently provided lower scores, then the program 110 may statistically adjust the scores upward. Similarly, if one clinician consistently provided higher scores, then the program 110 may statistically adjust the scores downward. According to one embodiment, a bell-shaped curve distribution may be derived.

In operation 350, the QA scorecard program 110 may present the clinician's survey results to the radiologist along with other information sources, including the patient's data profile in the HIS 10, RIS 20, PACS 30, EMR or other information sources in order to determine the radiologist's diagnostic accuracy. According to one embodiment of the invention, the QA scorecard program 110 may search information sources for pertinent data. According to one embodiment of the invention, the QA scorecard program 110 may customize natural language processing (NLP) programs for the radiology domain to identify "key concepts" in radiology reports and search the information databases for correlating data. According to one embodiment of the invention, pertinent data may be extracted from laboratory and pathology data; health and physical data; discharge summaries; consultations; patient-specific demographic data; genomic data; and other data.

According to one embodiment, structured reporting enable the QA scorecard program 110 to search reporting databases on multiple levels, including institutional, local, national, and/or international to establish community and national norms for context-specific diagnostic accuracy measures. According to one embodiment, the QA scorecard program 110 may access QA consortiums that include groups of qualified multi-specialty teleradiology providers that may independently review anonymized imaging studies and associated reports for diagnostic accuracy. According to one embodiment, the QA scorecard program 110 may enable the review process to be randomized and subject to external validation by a governing QA body, which may oversee the certification of these multi-specialty QA providers. According to one embodiment, the QA scorecard program 110 would provide each individual radiologist, radiology group, and hospital or imaging center with QA scores for diagnostic accuracy based on this cumulative data. According to one embodiment, the QA scorecard program 110 may incorporate this data into the radiologist QA Scorecard, which may be made available for public access to the benefit of the entire consumer group.

In operation 352, the QA scorecard program 110 may analyze QA metrics for adherence to community standards or professional guidelines. According to one embodiment, the QA scorecard program 110 may provide user recommendations for increasing consistency in practice patterns so that radiology providers may be held to the same standards. According to one embodiment, community standards may be applied to provide uniformity to imaging service utilization; imaging study protocols; application of ancillary technologies, such as computer aided detection software (CAD); and reporting/communication profiles, among other areas.

Regarding image service utilization, a uniform set of appropriateness criteria may be defined that take into account a multitude of clinical and imaging variables and provide objective feedback data to physicians in order to maximize patient safety, cost, and diagnostic accuracy. According to one embodiment of the invention, the metrics module 232 may generate a QA score for the users based on an evaluation of adherence to community standards.

In operation 354, the QA scorecard program 110 may receive the complication rate and adverse outcomes as they relate to the medical imaging exams and procedures. According to one embodiment of the invention, the imaging QA database may contain objective data that relates to complications, such as contrast-induced nephrotoxicity and allergic reactions; iatrogenic trauma in the setting of invasive procedures; and adverse patient outcomes due to delayed/missed radiological diagnoses; among other complications. The metrics module 232 may search the QA database and analyze each individual radiologist's QA metrics as they relate to the specific type of exam, clinical indication, patient profile, and complication that ensued. According to one embodiment of the invention, this information may be presented as an educational resource for referring clinicians, patients, and third party payers. According to one embodiment of the invention, any educational and training programs that are performed by the radiologist as a result of the documented complication may be recorded in the QA database and factored into the analysis, so that radiologists have a mechanism to improve their QA scores with remedial education and training.

In operation 356, the QA scorecard program 110 may perform trend analysis of radiologist diagnostic accuracy. The trend analysis may be evaluated on an individual patient and patient group basis, with patient groups classified according to demographics, medical histories, and clinical profiles. According to one embodiment of the invention, the QA scorecard program 110 may perform trend analysis to identify specific trends in diagnostic accuracy. Since patient, institution, and clinical indication are unique, they should be taken in the overall context of multiple data points. For example, if a radiologist misdiagnoses a single patient than it is recorded and taken into context. If, on the other hand, that same radiologist repeatedly misdiagnoses on multiple patients, then the overall trend is one which identified a need for intervention, such as in the form of education. According to one embodiment, the QA scorecard program 110 may correlate misdiagnostic data trends with local, regional, and national norms. The QA scorecard program 110 may provide data-driven feedback to each radiologist relative to their peer group for educational purposes.

In operation 358, the QA scorecard program 110 may perform periodic evaluations of interpreting radiologists based on education and training. According to one embodiment, education and training may include factors, such as board certification; residency and fellowship training; specialty certification; continuing medical education (CME); and specialized training in the specific area of interpretation; among other factors. For example, as new applications within radiology are introduced (e.g. PET, CT angiography, cardiac MRI), the QA scorecard program 110 may increase education credit QA scores for radiologists that perform these imaging exams based on completion of documented CME programs that specifically address these applications. According to another embodiment, the QA scorecard program 110 may increase education credit QA scores for radiologists that actively contribute to research. Research credits may include active participation in clinical trials; submission of cases to on-line teaching files (e.g. MIRC); co-authoring articles in the peer review literature; or providing financial contributions.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of generating a quality assurance score, comprising:
   obtaining and storing information on a patient, in at least one patient profile, in at least one database of a client computer or a server computer of a computer system;
   displaying, on a display, at least one image from an imaging exam stored with said at least one patient profile;
   receiving and storing in said at least one database, an image quality evaluation of said imaging exam by a user;
   providing a survey of a predetermined list of questions to a predetermined group of respondents, including said user, whom includes at least a technologist and a radiologist, via an electronic communication mechanism;
   receiving and storing responses to said predetermined list of questions, in said at least one database, including said responses on at least said image quality evaluation, from said predetermined group of respondents;
   determining a diagnostic accuracy of at least one of said predetermined group of respondents by analyzing said responses using said computer system, including said responses on at least said image quality evaluation, along with said at least one patient profile; and
   generating a quantifiable quality assurance score using said computer system, indicating a measure of quality assurance compliance of at least one of said predetermined group of respondents, wherein said quality assurance score includes a time response calculated by said computer system, of at least a time taken by said respondent radiologist from receipt to review of said imaging examination, and at least a time taken in reviewing said imaging exam by said respondent radiologist.

2. The method according to claim 1, further comprising:
   performing an access authorization procedure on said user at said client computer, prior to retrieving said information from said at least one database;
   alerting said user via electronic means at said client computer, when less than full access privileges are associated with said user;
   initiating a reduction in privileges at said client computer for a user, for at least one of failure to follow a predefined protocol, frequent misdiagnosis of an ailment, failure to follow a cost-effective treatment plan, or failure to complete continuing medical education;
   identifying and recommending at least one re-credentialing program to said user, using said computer system when said privileges are reduced; and
   restoring full access privileges at said client computer, to said user, after completion of said re-credentialing program;
   wherein said at least one re-credentialing program includes at least one of board certification; residency and fellowship training; specialty certification; continuing medical education (CME); or specialized training in a specific area of interpretation.

3. The method according to claim 2, further comprising:
   granting a grace period for regaining full privileges to said user before all of said access privileges are revoked at said client computer;
   wherein said grace period is calculated by one of a number of log-ins or days by said computer system,
   wherein said number of log-ins or days is determined by a frequency of occurrence of predetermined triggers, including at least one of a severity of an error, or an amount of time required to complete a re-credentialing program.

4. The method according to claim 2, wherein said information includes an imaging data sheet; and further comprising:
   completing said imaging data sheet using said computer system, with data including past medical and surgical history, including at least one of prior imaging exams and results, including those performed at outside facilities; current clinical problems; pertinent findings on a physical exam; pertinent laboratory or pathology data; procedural findings; operative or consultation notes; clinical testing; technical information related to a previous imaging exam performed; technologist observations including pertinent findings and measurements; technologist notes including complications and imaging exam limitations.

5. The method according to claim 2, further comprising:
   completing said imaging sheet using said computer system, with data including all pertinent clinical data elements related to a diagnosis being evaluated, including at least one of a past medical and surgical history; allergies; reactions to contrast media used in medical imaging; risk factors, including family history and tumor markers; non-imaging data, including laboratory and clinical testing; pathology; clinical indication and presumptive diagnosis; findings on physical examination; historical imaging data, or outside imaging exams and findings.

6. The method according to claim 5, further comprising:
   receiving user-created patient profiles for said imaging data sheet at said client computer;
   storing a customized imaging data sheet on said patient in said at least one database;
   recording a time-stamp each time a new entry or modification is made to said imaging data sheet using said computer system; and
   displaying on said display, said user's individual preferences based on said customized imaging data sheet stored by said user.

7. The method according to claim 1, further comprising:
   displaying on said display, a computerized physician order entry (CPOE) to the user for clarification of discrepancies or clinical questions; and
   storing corrections of said discrepancies in said at least one database.

8. The method according to claim 7, further comprising:
   identifying clinically unexpected or emergent findings during the course of an imaging exam interpretation using said computer system; and
   alerting at least one other user from said predetermined group of respondents to said findings, wherein said alert is sent via any type of electronic communication; and
   wherein when said clinically unexpected or emergent findings are not present, said image is presented to said user on said display, with a predetermined display protocol.

9. The method according to claim 8, further comprising:
   creating a time stamp of said electronic communication using said computer system;

recording, with said time stamp, in said at least one database, at least one of a scheduling time of said imaging exam; an arrival of said patient; a start and a completion time of said imaging exam; a transmission of said imaging exam to a PACs for interpretation; an opening time of said imaging exam by the user; a closing time of said imaging exam; a time that a report is dictated; and a signing time of an imaging report;

storing, in said at least one database, said alert; and generating said quality assurance score using an analysis of said alert, using said computer system.

10. The method according to claim 9, further comprising generating said quality assurance score using said computer system, said instructions which including receiving and storing data in said at least one database, said data which includes at least one of information on a time from receipt of said image from said imaging exam to receipt by at least one respondent of said predetermined group of respondents; specific components of said image reviewed by said respondent radiologist; an image open time and image close time; a time incurred by a respondent clinician in responding to said alert; said type of said electronic communication; acknowledgements of receipt of said alert by said predetermined group of respondents; bi-directional consultations held between individual of said group of respondents; a time taken to initiate treatment; tracking of follow-up recommendations; clinician satisfaction; and referral patterns.

11. The method according to claim 10, further comprising:

providing access for a respondent clinician at said client computer, to enter data electronically into an electronic medical report (EMR) in said least one database;

tracking clinician actions using said computer system, including recording progress notes, consultations held, ordering of clinical tests and imaging studies, and treatment options entered into said client computer; and tracking said data and actions for analysis and generation of said quality assurance score using said computer system.

12. The method according to claim 11, further comprising:

enabling said respondent radiologist to dynamically manipulate said image on said display, and to highlight at least one key image from a large data set on said display;

wherein said manipulation includes at least one of a reconstruction images in multiple imaging of planes or image processing of said image.

13. The method according to claim 1, further comprising:

receiving data from said radiologist at said client computer, on a rating of said image quality and on a finding of whether said image quality is acceptable for review;

wherein said image quality evaluation is performed by one of said radiologist or a clinician using a Likert scale.

14. The method according to claim 13, further comprising:

using said computer system to request that said imaging exam be rescheduled when said image quality is poor as analyzed by said computer system; and using said computer system to provide at least one recommendation to a technologist for improving a future imaging exam having similar parameters, said recommendation being provided by electronic means;

wherein said recommendation includes at least one of producing alternate image examinations or adjusting a dosage.

15. The method according to claim 1, further comprising:

receiving a structured text report at said client computer, that is correlated with said imaging exam by said computer system; and database mining said reports which contain a standardized lexicon, such that community and nationwide norms are established using said computer system.

16. The method according to claim 15, wherein reporting templates are used by said computer system to create consistent and reproducible data which are used in a statistical analysis by said computer system, said statistical analysis which is performed by said computer system on a predetermined schedule, and used in generation of said quality assurance score by said computer system;

wherein said quality assurance score provides questions for said user to identify hidden biases, and to adjust said quality assurance score based on answers to said questions.

17. The method according to claim 16, further comprising:

updating at least one data profile of said patient with said structured text report in said at least one database;

wherein said data profile is at least one of an electronic medical record (EMR), a hospital information system (HIS), and a radiology information system (RIS).

18. The method according to claim 17, further comprising:

using said computer system to computer search databases at institutional, local, national, and international levels to establish community and national norms for context-specific diagnostic accuracy measures; and providing said user at said client computer, with said quality assurance score for diagnostic accuracy based on cumulative data obtained from all said databases.

19. The method according to claim 18, further comprising:

analyzing quality assurance metrics for adherence of said user to community standards or professional guidelines using said computer system;

wherein said community standards may be applied to provide uniformity to at least one of imaging service utilization; imaging study protocols; application of ancillary technologies including computer aided detection software (CAD); and reporting/communication profiles; and including said analysis using said computer system, including said image quality evaluation, in a trending analysis performed by said computer system.

20. The method according to claim 19, further comprising:

obtaining a complication rate and adverse outcomes related to said imaging exam and imaging procedures from said at least one database using said computer system;

correlating misdiagnostic trends with local, regional, and national norms using said computer system;

performing trending analysis using said computer system, of said user's diagnostic accuracy; and providing all said outcomes of said trending analysis, using said computer system, to said user at said client computer, for performance improvement and to third parties as an educational resource.

21. A computer system for generating a quality assurance score, comprising:

at least one memory containing at least one program comprising the steps of:

obtaining and storing information on a patient, in at least one patient profile, in at least one database of a client computer or a server computer of a computer system;

displaying, on a display, at least one image from an imaging exam stored with said at least one patient profile;

receiving and storing in said at least one database, an image quality evaluation of said imaging exam by a user;

providing a survey of a predetermined list of questions to a predetermined group of respondents, including said user, whom includes at least a technologist and a radiologist, via an electronic communication mechanism;

receiving and storing responses to said predetermined list of questions, in said at least one database, including said responses on at least said image quality evaluation, from said predetermined group of respondents;

determining a diagnostic accuracy of at least one of said predetermined group of respondents by analyzing said responses using said computer system, including said responses on at least said image quality evaluation, along with said at least one patient profile; and generating a quantifiable quality assurance score using said computer system, indicating a measure of quality assurance compliance of at least one of said predetermined group of respondents, wherein said quality assurance score includes a time response calculated by said computer system, of at least a time taken by said respondent radiologist from receipt to review of said imaging examination, and at least a time taken in reviewing said imaging exam by said respondent radiologist; and a processor for running said program.

22. A non-transitory computer-readable medium containing instructions for generating a quality assurance scorecard, comprising:

obtaining and storing information on a patient, in at least one patient profile, in at least one database of a client computer or a server computer of a computer system;

displaying, on a display, at least one image from an imaging exam stored with said at least one patient profile;

receiving and storing in said at least one database, an image quality evaluation of said imaging exam by a user;

providing a survey of a predetermined list of questions to a predetermined group of respondents, including said user, whom includes at least a technologist and a radiologist, via an electronic communication mechanism;

receiving and storing responses to said predetermined list of questions, in said at least one database, including said responses on at least said image quality evaluation, from said predetermined group of respondents;

determining a diagnostic accuracy of at least one of said predetermined group of respondents by analyzing said responses using said computer system, including said responses on at least said image quality evaluation, along with said at least one patient profile; and generating a quantifiable quality assurance score using said computer system, indicating a measure of quality assurance compliance of at least one of said predetermined group of respondents, wherein said quality assurance score includes a time response calculated by said computer system, of at least a time taken by said respondent radiologist from receipt to review of said imaging examination, and at least a time taken in reviewing said imaging exam by said respondent radiologist.

* * * * *